US012714447B2

(12) United States Patent
Moy et al.

(10) Patent No.: US 12,714,447 B2
(45) Date of Patent: Aug. 25, 2026

(54) ASPIRATION DEVICES INCLUDING FISHMOUTH SHAPED ASPECTS

(71) Applicant: Switchback Medical LLC, Brooklyn Park, MN (US)

(72) Inventors: Joseph Moy, Shorewood, MN (US); Toukao Vang, Brooklyn Center, MN (US); Randy Beyreis, Andover, MN (US); Brady Hatcher, Rogers, MN (US)

(73) Assignee: SWITCHBACK MEDICAL LLC, Brooklyn Park, MN (US)

( * ) Notice: Subject to any disclaimer, the term of this patent is extended or adjusted under 35 U.S.C. 154(b) by 0 days.

(21) Appl. No.: 19/292,259

(22) Filed: Aug. 6, 2025

(65) Prior Publication Data

US 2026/0047854 A1 Feb. 19, 2026

Related U.S. Application Data

(60) Provisional application No. 63/682,676, filed on Aug. 13, 2024.

(51) Int. Cl.
*A61B 17/22* (2006.01)

(52) U.S. Cl.
CPC .... *A61B 17/22* (2013.01); *A61B 2017/22079* (2013.01)

(58) Field of Classification Search
CPC .......... A61B 17/22; A61B 2017/22079; A61B 2017/22081; A61B 2017/2215; A61B 2218/002; A61B 2218/001; A61B 2218/007; A61B 17/22012; A61B 2017/22035; A61M 1/84; A61M 1/87
See application file for complete search history.

(56) References Cited

U.S. PATENT DOCUMENTS 4,850,354 A * 7/1989 McGurk-Burleson ....................... A61B 17/32002 30/240
2015/0080853 A1 3/2015 Smalling
2018/0339131 A1 11/2018 Muse et al.
2020/0155178 A1 5/2020 Culbert et al.
2021/0393277 A1 12/2021 Vale et al.

FOREIGN PATENT DOCUMENTS

EP 3335647 B1 * 1/2022 ............ A61M 29/00
KR 1020230059434 A 5/2023

* cited by examiner

*Primary Examiner* — Katherine M Shi
(74) *Attorney, Agent, or Firm* — Gallium Law; Jacob Panangat; Justin Schwechter

(57) ABSTRACT

Included in the present disclosure is a medical device, including a catheter, including an aspiration lumen. In some embodiments, the medical device includes an aspiration head located at a distal end of the catheter, the aspiration head including a fishmouth.

20 Claims, 21 Drawing Sheets

ASPIRATION DEVICES INCLUDING FISHMOUTH SHAPED ASPECTS

CROSS-REFERENCE TO RELATED APPLICATIONS

The entire contents of the following application are incorporated herein: U.S. Provisional Patent Application Ser. No. 63/682,676; filed on Aug. 13, 2024; and entitled NEURO-INTERVENTIONAL CATHETER SYSTEMS AND METHODS.

FIELD OF TECHNOLOGY

The present disclosure relates to the removal of occlusions or other unwanted matter from vessels, ducts, cavities, and lumens of an organism.

BACKGROUND

Clot aspiration is a widely used technique in neurovascular interventions, particularly in the treatment of acute ischemic stroke caused by large vessel occlusion. The procedure involves the mechanical removal of a thrombus (blood clot/occlusion) from cerebral arteries using a suction catheter. This method is often performed as part of mechanical thrombectomy procedures and can be used alone or in combination with stent retrievers. By re-establishing blood flow quickly, clot aspiration helps limit the extent of brain damage and improves the chances of neurological recovery. It is typically performed through minimally invasive endovascular access, most commonly via the femoral or radial artery, allowing interventional neuroradiologists or neurointerventional surgeons to navigate catheters into the cerebral vasculature under image guidance.

SUMMARY

Included in the present disclosure is a medical device, including a catheter, including an aspiration lumen. In some embodiments, the medical device includes an aspiration head located at a distal end of the catheter, the aspiration head including a fishmouth.

According to some embodiments, the aspiration head is configured to facilitate a prevention or reduction of snags on an intima of a vessel of a patient during delivery of the catheter to a target treatment site. The aspiration head may be configured to optimize contact with an obstruction in the target treatment site.

In some embodiments, the fishmouth defines a perimeter including two peaks located at opposite ends of the aspiration head from one another. According to some embodiments, the perimeter includes two valleys each located between the two peaks about the perimeter, the two valleys located at opposite ends of the aspiration head from one another.

At least one of the two valleys may include an area of material weakness, such that, when aspiration is performed through the catheter, the two peaks are pulled inward with respect to one another. In some embodiments, the medical device further includes a hinge located on an inside or an outside of i) one or ii) both of the two valleys, the hinge configured to permit the two peaks to be pulled inward with respect to one another while aspiration is performed through the catheter.

According to some embodiments, the two peaks extend from the two valleys at an angle from about one degree to about one hundred and seventy-nine degrees.

The aspiration head may be made from a polymer. In some embodiments, the catheter is made from i) stainless steel, ii) nitinol, iii) Polytetrafluoroethylene (PTFE), iv) polymer, or v) combinations thereof.

According to some embodiments, the aspiration head has an inner diameter between about thirty thousandths of an inch and about one hundred and twelve thousandths of an inch.

The medical device may further include a sheath including a delivery lumen through which the catheter is configured to extend.

In some embodiments, the fishmouth is a catheter fishmouth, and the sheath includes a sheath aspiration head located at a distal end of the sheath, the sheath aspiration head including a sheath fishmouth. According to some embodiments, the sheath aspiration head is configured to facilitate a prevention or reduction of snags on the intima of the vessel of a patient during delivery of the sheath to the target treatment site. The sheath aspiration head may be configured to optimize contact with an obstruction in the target treatment site.

In some embodiments, the two peaks are two catheter peaks, and the two valleys are two catheter valleys. According to some embodiments, the sheath fishmouth defines a perimeter having two sheath peaks located at opposite ends of the sheath aspiration head from one another. The sheath perimeter may have two sheath valleys each located between the two sheath peaks about the sheath fishmouth perimeter, the two sheath valleys located at opposite ends of the sheath aspiration head from one another.

In some embodiments, at least one of the two sheath valleys includes an area of material weakness, such that, when aspiration is performed through the sheath, the two sheath peaks are pulled inward with respect to one another. According to some embodiments, the medical device further includes a hinge located on an inside or an outside of i) one or ii) both of the two valleys, the hinge configured to permit the two sheath peaks to be pulled inward with respect to one another while aspiration is performed through the sheath.

The two sheath peaks may extend from the two valleys at an angle from about one degree to about one hundred and seventy-nine degrees.

In some embodiments, the sheath aspiration head is made from a polymer. According to some embodiments, the sheath is made from i) stainless steel, ii) nitinol, iii) PTFE, iv) polymer, or v) combinations thereof.

The sheath aspiration head may have an inner diameter between about thirty thousandths of an inch and about one hundred and twelve thousandths of an inch.

Also included in the present disclosure is a method, including delivering a catheter including an aspiration lumen and an aspiration head located at a distal end of the catheter to a target treatment site, wherein the aspiration head includes a fishmouth. In some embodiments, the method includes aspirating, via the aspiration lumen, an occlusion from the target treatment site. According to some embodiments, the method includes removing the catheter from the target treatment site.

The aspiration head may define a perimeter having two peaks located at opposite ends of the aspiration head from one another. In some embodiments, the perimeter has two valleys each located between the two peaks about the perimeter, the two valleys located at opposite ends of the aspiration head from one another. According to some embodiments, the method further includes optimizing contact with the obstruction in the target treatment site.

At least one of the two valleys may include an area of material weakness. In some embodiments, the method further includes pulling the two peaks inward with respect to one another via an aspiration force. According to some embodiments, a hinge is located on an inside or an outside of i) one or ii) both of the two valleys. The method may further include pulling the two peaks inward with respect to one another via an aspiration force.

Also included in the present disclosure is a method, including delivering a sheath including a delivery lumen and a sheath aspiration head located at a distal end of the sheath to a target treatment site, wherein the sheath aspiration head includes a fishmouth. In some embodiments, the method includes aspirating, via the delivery lumen, an occlusion from the target treatment site. According to some embodiments, the method includes removing the sheath from the target treatment site.

The aspiration head may define a perimeter having two peaks located at opposite ends of the sheath aspiration head from one another. In some embodiments, the perimeter has two valleys each located between the two peaks about the aspiration head perimeter, the two valleys located at opposite ends of the sheath aspiration head from one another. According to some embodiments, the method further includes optimizing contact between the aspiration head and an obstruction in the target treatment site.

At least one of the two valleys may include an area of material weakness. In some embodiments, the method further includes pulling the two peaks inward with respect to one another via an aspiration force. According to some embodiments, a hinge is located on an inside or an outside of i) one or ii) both of the two valleys. The method may further include pulling the two peaks inward with respect to one another via an aspiration force.

In some embodiments, the fishmouth is a sheath fishmouth and the aspiration head is a sheath aspiration head. According to some embodiments, the method further includes delivering a catheter including an aspiration lumen and a catheter aspiration head located at a distal end of the catheter to a second target treatment site via the delivery lumen, wherein the catheter aspiration head includes a catheter fishmouth.

Delivering the catheter to the second target treatment site may occur after delivering the sheath to the target treatment site.

In some embodiments, the method further includes aspirating, via the aspiration lumen, the occlusion or a second occlusion from the second target treatment site.

According to some embodiments, the method further includes removing the catheter from the second target treatment site. Removing the catheter from the second target treatment site may occur prior to removing the sheath from the target treatment site.

In some embodiments, the two peaks are two sheath peaks, the two valleys are two sheath valleys, and the catheter aspiration head defines a perimeter having two catheter peaks located at opposite ends of the aspiration head from one another. According to some embodiments, the perimeter has two catheter valleys each located between the two catheter peaks about the catheter aspiration head perimeter, the two catheter valleys located at opposite ends of the aspiration head from one another. The method may further include optimizing contact between the catheter aspiration head and an obstruction in the second target treatment site.

In some embodiments, at least one of the two catheter valleys includes an area of material weakness, the method further including pulling the two catheter peaks inward with respect to one another via an aspiration force. According to some embodiments, the hinge is a sheath hinge and the catheter further includes a catheter hinge located on an inside or an outside of i) one or ii) both of the two catheter valleys. The method may further include pulling the two catheter peaks inward with respect to one another via an aspiration force.

The foregoing, and other features and advantages of the invention, will be apparent from the following, more particular description of the preferred embodiments of the invention, the accompanying drawings, and the claims.

BRIEF DESCRIPTION OF THE DRAWINGS

These and other features, aspects, and advantages are described below with reference to the drawings, which are intended to illustrate, but not to limit, the invention. In the drawings, like characters denote corresponding features consistently throughout similar embodiments.

DETAILED DESCRIPTION

Although specific examples are disclosed below, inventive subject matter extends beyond the specifically disclosed examples to alternative examples and/or uses and modifications and equivalents thereof. Thus, the scope of the claims appended hereto is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations, in turn, in a manner that may be helpful in understanding specific examples; however, the order of description should not be construed to imply that these operations are order-dependent. Additionally, the structures, systems, and/or devices described herein may be embodied as integrated or separate components.

For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

Figure 1:
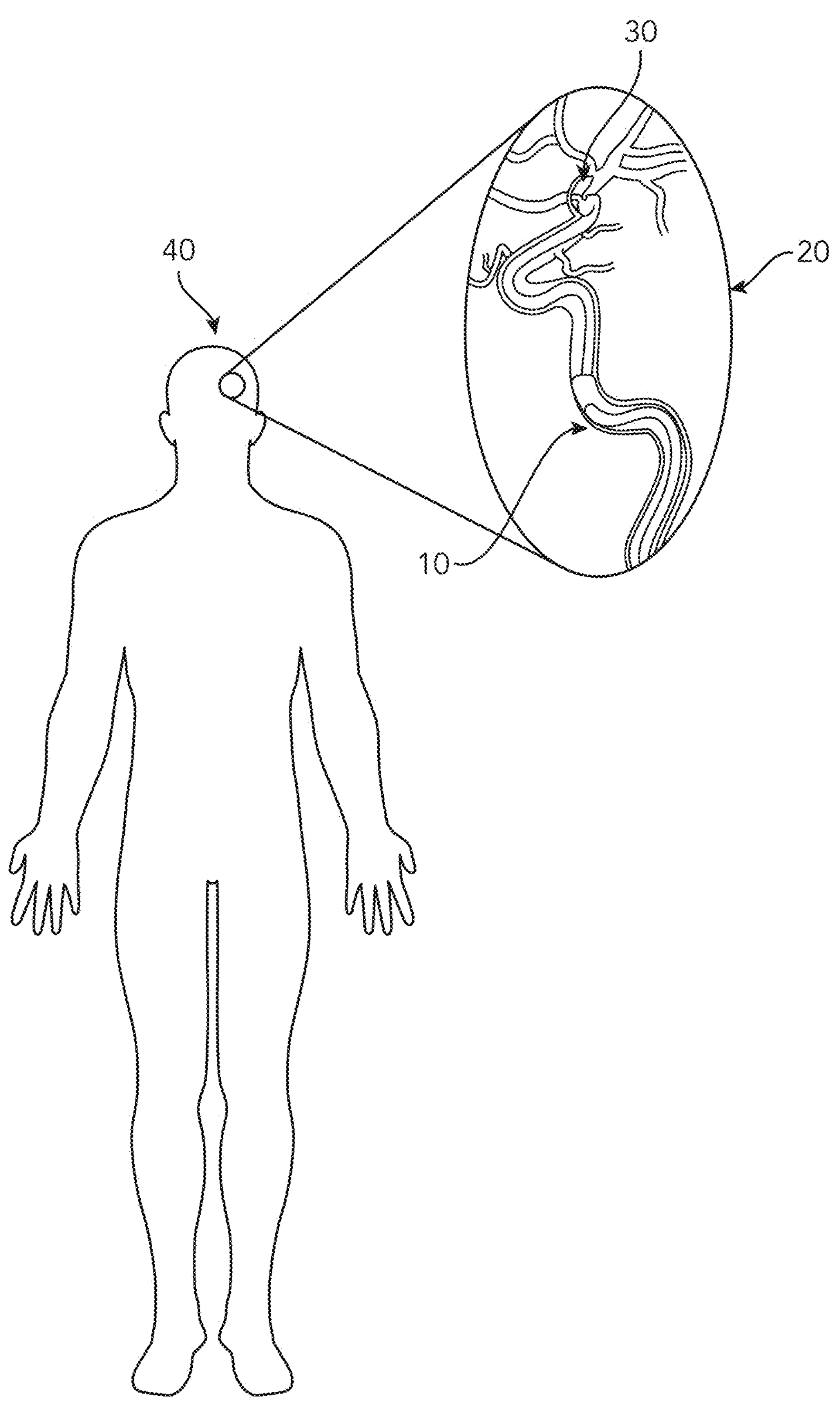
FIG. 1 illustrates a diagrammatic view of a medical device as it may appear in a patient's vasculature, and an example location within the patient.

FIG. 1 illustrates a diagrammatic view of a medical device 10 as it may appear in a patient's 40 vasculature. The medical device 10 may be an aspiration catheter (as shown and described in FIGS. 3-6 below), or an aspiration catheter and a delivery sheath (as shown and described in FIGS. 7-12 below).

A distal end of medical device 10 may be inserted through a patient's 40 vasculature until reaching a target treatment site 20. In some embodiments, the target treatment site 20 includes an occlusion 30 which the medical device 10 is intended to retrieve, such as via aspiration.

Figure 2:
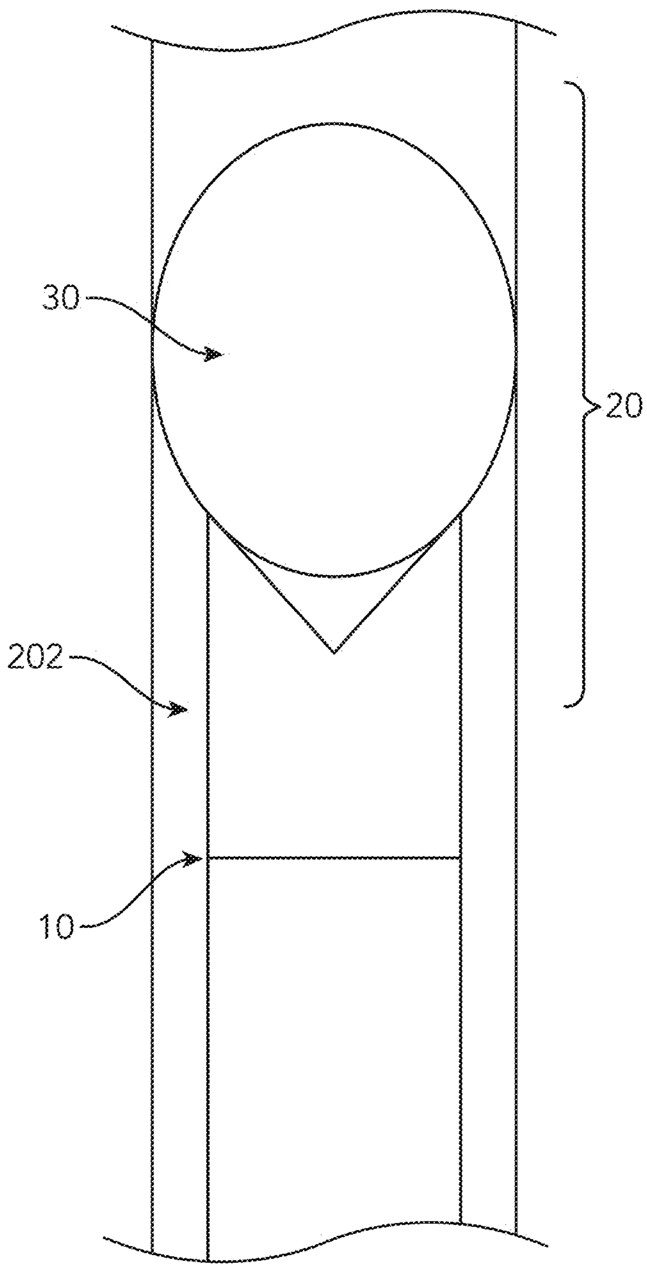
FIG. 2 illustrates a diagrammatic side view of a medical device interacting with an occlusion, according to some embodiments.

FIG. 2 illustrates a diagrammatic side view of a medical device 10 interacting with an occlusion 30, according to some embodiments. In some embodiments, the medical device includes an aspiration head 202 including a fishmouth shape, which is exaggerated for illustration purposes throughout the present figures. The fishmouth may also be considered a saddle, or hyperbolic paraboloid. The aspiration head 202 is illustrated within a target treatment site 20 interacting with an obstruction 30.

Because of the generally asymmetric nature of naturally occurring occlusions 30 within vessels, flat-faced/planar profiled aspiration devices fail to gain a strong grasp of the occlusion, only making contact with the occlusion at certain spots about the perimeter of the aspiration device.

One solution to this problem has been to create an angled aspiration device, which is capable of making increased contact with the occlusion 30 due to both the angle at which it meets the occlusion 30, as well as the increased perimeter inherent to an angled cut through a cylinder versus a flat cut through a cylinder.

However, angled aspiration devices present problems as well. Due to the shape of an angled cut through a cylinder, a sharp point is left at one side of the device. This sharp point may unintentionally abrade or pierce the intima of a vessel as the device is delivered to its treatment area. Additionally, an angled medical device may snare on a vascular junction, for instance, an ophthalmic vein, while being delivered to an intracranial vasculature.

The present disclosure pertains to seeking the benefits of ease of deliverability as well as optimal contact with an occlusion 30, while minimizing or completely eliminating the potential for abrading/piercing the intima of a vessel or snaring on a vascular junction during delivery. The medical devices herein accomplish this through the use of a fishmouth design, which helps prevent and/or reduce the risk of sharp points for piercing the intima, while also increasing the perimeter of the contact portion of the medical device 10, which in turn may increase the amount of contact made with the occlusion 30, thus improving aspiration capabilities. For example, the fishmouth may be oriented such that a valley (as described herein) is located closest to a vascular junction so that the peaks do not interact with such a junction. In additional or alternative embodiments, the peaks may be rounded enough that snagging on a vascular junction is reduced as a concern.

Figure 3:
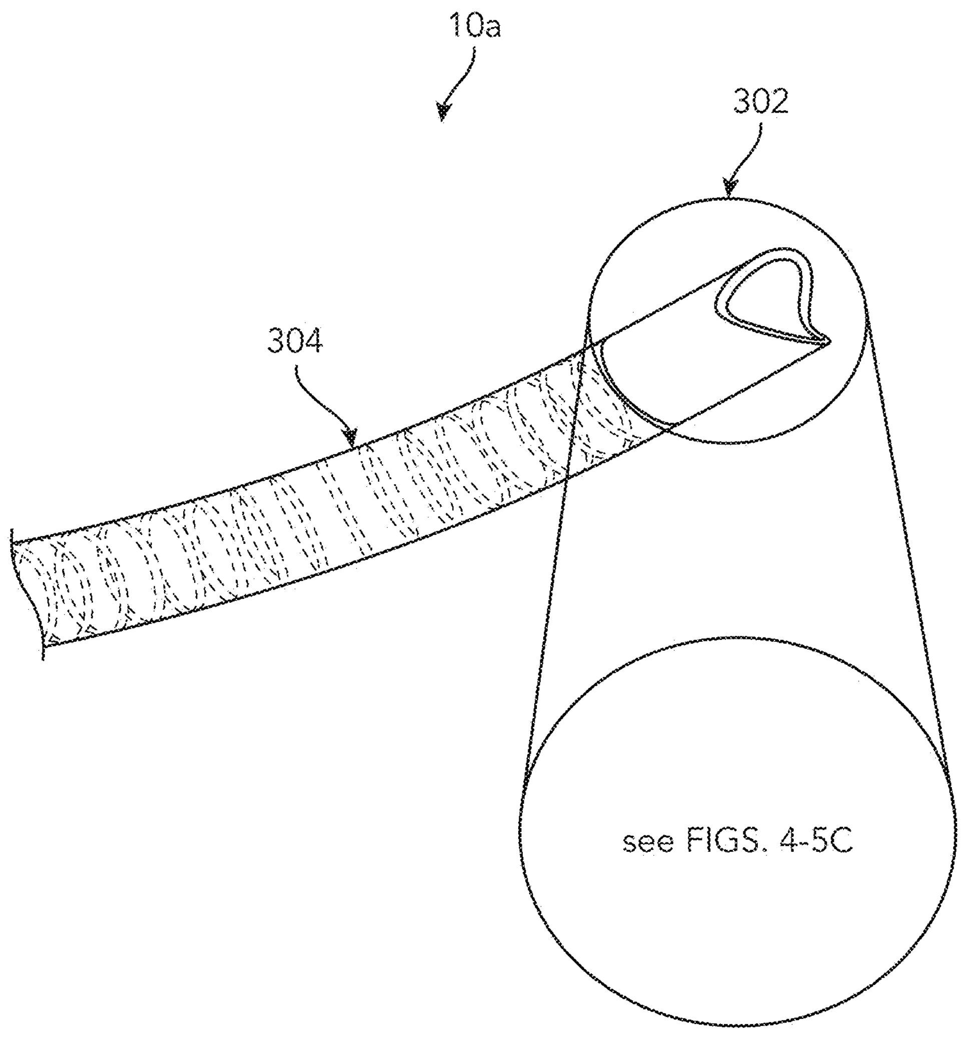
FIG. 3 illustrates a perspective view of a medical device including an aspiration head, according to some embodiments.
Figure 4:
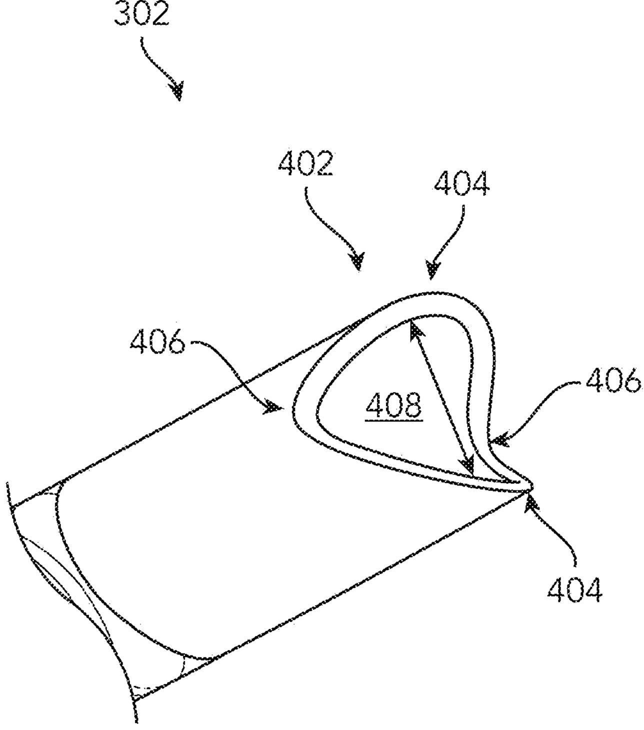
FIG. 4 illustrates a perspective view of the aspiration head of FIG. 3, according to some embodiments.

FIG. 3 illustrates a perspective view of a medical device 10*a* including an aspiration head 302, according to some embodiments. In this embodiment, and the embodiments of FIGS. 4-6, the medical device 10*a* includes a catheter 304, and an aspiration head 302 with a fishmouth at the distal end. The aspiration head may be made from a polymer. The catheter may be made from i) stainless steel, ii) nitinol, iii) PTFE, iv) polymer, or v) combinations thereof FIG. 4 illustrates a perspective view of the aspiration head 302 of FIG. 3, according to some embodiments. FIG. 4 illustrates in more detail the fishmouth 402 profile, showing the peaks 404 and valleys 406 which make up the fishmouth 402 profile. The peaks 404 may also be considered "jaws" (such as "teeth" of a fishmouth). Generally, the fishmouth 402 will include two peaks 404 opposite one another, and two valleys 406 opposite one another, the valleys 406 between the peaks 404 about the perimeter of the fishmouth 402. In additional or alternative embodiments, more peaks and valleys may be included, creating an appearance akin to a saw wrapped in a circle.

Also illustrated in FIG. 4 is the inner diameter (ID) 408 of the aspiration head 302. The ID 408 of the aspiration head 302 may be from about thirty thousandths of an inch to about one hundred and twelve thousandths of an inch. The aspiration head 302 may be chosen based on the ID 408 needed for the treatment of a vessel with a specific diameter, thereby maximizing the ID 408 of the aspiration head 302 that can be delivered through the vessel and contacting the occlusion. Additionally, an ID of the catheter 304 may be equal to or at least substantially equal to the ID of the aspiration head 302.

Figure 5A:
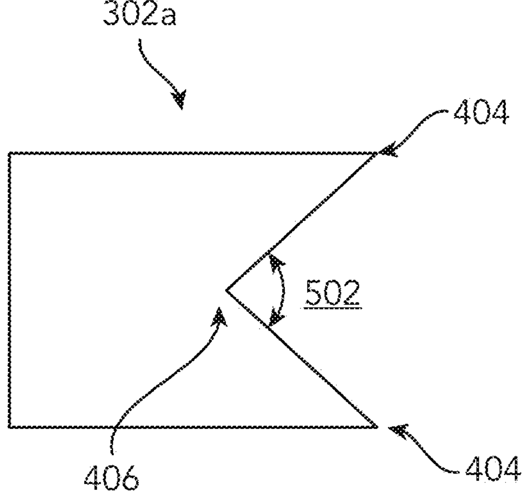
FIG. 5A illustrates a diagrammatic side view of an aspiration head, according to some embodiments.

FIG. 5A illustrates a diagrammatic side view of an aspiration head 302*a*, according to some embodiments. As shown in FIG. 4, the aspiration head 302*a* includes peaks 404 and valleys 406. While the peaks 404 and valleys 406 may be rounded for both ease of use and manufacture, they are represented as angular in FIGS. 5A-5C to facilitate the present disclosure.

As shown in FIG. 5A, the peaks 404 meet the valleys 406 at an angle of extension 502. This angle of extension 502 may be the same, or different, between different peaks 404 and different valleys 406. For the purposes of FIG. 5A, it is assumed that the angle of extension 502 between peaks 404 and the valleys 406 are the same.

The angle of extension 502 may be from about one degree to about one hundred and seventy-nine degrees. That is to say, any angle of extension 502 is considered in the present application between having an angle steep enough to include almost parallel lines, and having almost no angle. In smaller diameter embodiments, steeper angles may still permit the side walls to meet each other in such a way as to facilitate contact with an occlusion. Similarly, in larger diameter embodiments, shallower angles may meet each other in such a way so as to facilitate greater contact with an occlusion than a flat-faced profile.

Figure 5B:
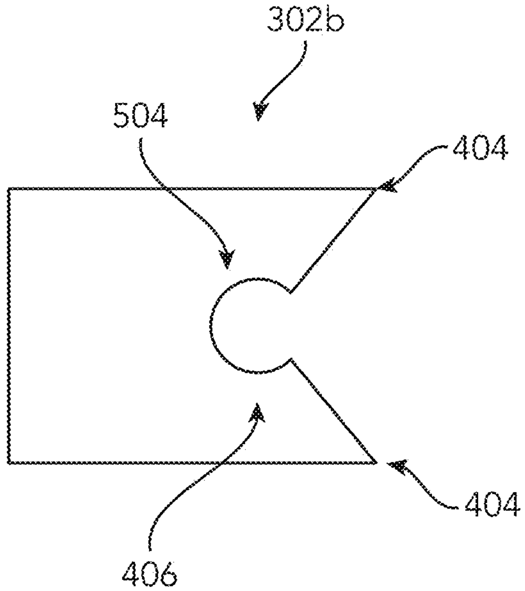
FIG. 5B illustrates a diagrammatic side view of another aspiration head, according to some embodiments.

FIG. 5B illustrates a diagrammatic side view of another aspiration head 302, according to some embodiments. In this embodiment, the aspiration head 302*b* continues to display the peaks 404 and valleys 406 of previous embodiments. However, in FIG. 5B, the valleys 406 include an area of material weakness 504. This area of material weakness 504 may be a specific notch, or cut out, in the valley 406 to allow the valley 406 to at least partially collapse inward. In additional or alternative embodiments, the area of material weakness 504 is a material that is different, and more malleable/frangible than the surrounding material of the aspiration head 302*b*.

In any embodiment, the area of material weakness 504 may permit the peaks 404 to collapse at least partially inward in response to a force, such as the force of aspiration delivered through the medical device 10*a*. In permitting the peaks 404 to collapse at least partially inward, greater contact with an occlusion 30 may occur, and, additionally or alternatively, a physical grip on the occlusion 30 may be had by the peaks 404.

Figure 5C:
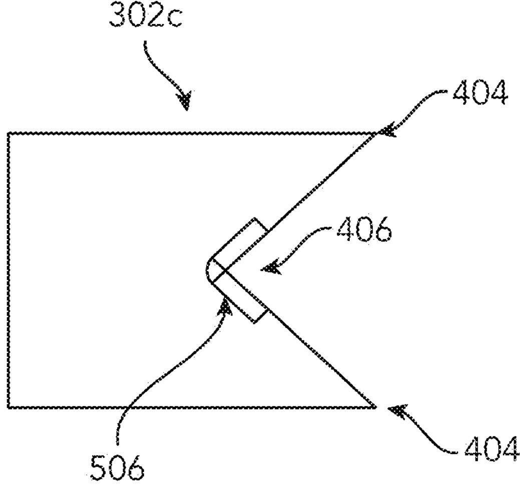
FIG. 5C illustrates a diagrammatic side view of another aspiration head, according to some embodiments.

FIG. 5C illustrates a diagrammatic side view of another aspiration head 302*c*, according to some embodiments. In this embodiment, the aspiration head 302*c* continues to display the peaks 404 and valleys 406 of previous embodiments. However, in FIG. 5C, the valleys 406 are coupled to/with a hinge 506. The hinge 506 may be combined with a material weakness in the valley 406, such as the area of material weakness 504 of FIG. 5B. In additional or alternative embodiments, the material from which the aspiration head 302*c* is made may be malleable enough to permit the peaks 404 to collapse inward under force.

In any such embodiments, the hinge 506 may facilitate both the initiation of collapse of the peaks 404 inward, as well as prevent too far of a collapse of the peaks 404 in the case of a substantially malleable material due to any inherent force of the hinge (i.e., spring constant in a provided spring in the hinge 506) as well as a maximum permitted closure of the hinge 506. In permitting the peaks 404 to collapse at least partially inward, greater contact with an occlusion 30 may occur, and, additionally or alternatively, a physical grip on the occlusion 30 may be had by the peaks 404.

Figure 6:
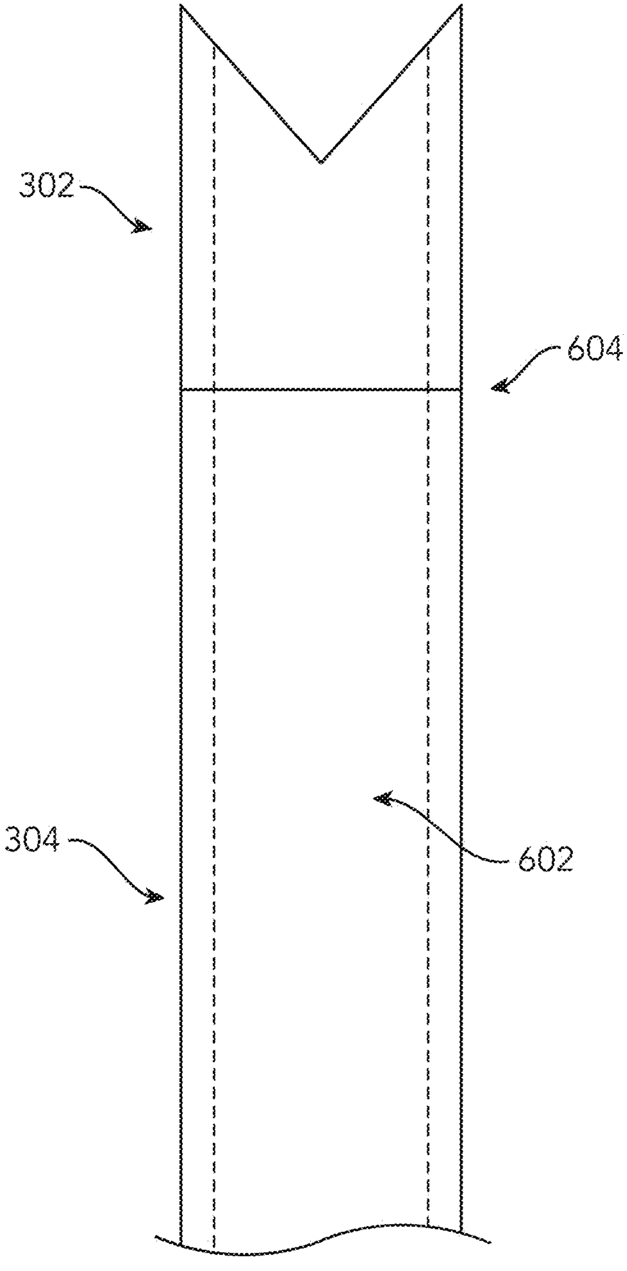
FIG. 6 illustrates a diagrammatic side view of the medical device of FIG. 3, according to some embodiments.

FIG. 6 illustrates a diagrammatic side view of the aspiration device 10*a* of FIG. 3, according to some embodiments. As shown in FIG. 6, the aspiration device 10*a* includes the aspiration head 302 as well as the catheter 304. Extending through both of the catheter 304 and the aspiration head 302, an aspiration lumen 602 is shown. The aspiration lumen 602 may be the lumen through which an aspiration force is provided in order to aspirate an occlusion 30 from a target treatment site 20.

Also shown in FIG. 6 is a distal end 604 where the aspiration head 302 couples to the catheter 304. In some embodiments, the distal end 604 is the distal end 604 of the catheter 304. In additional or alternative embodiments, the aspiration head 302 and the catheter 304 are a single structure. In such embodiments, distal end 604 represents a portion of the medical device 10*a* where the aspiration head 302 is considered to begin (i.e., the portion of the medical device 10*a* including peaks 404 and valleys 406) and where the catheter 304 portion is considered to terminate.

Figure 7:
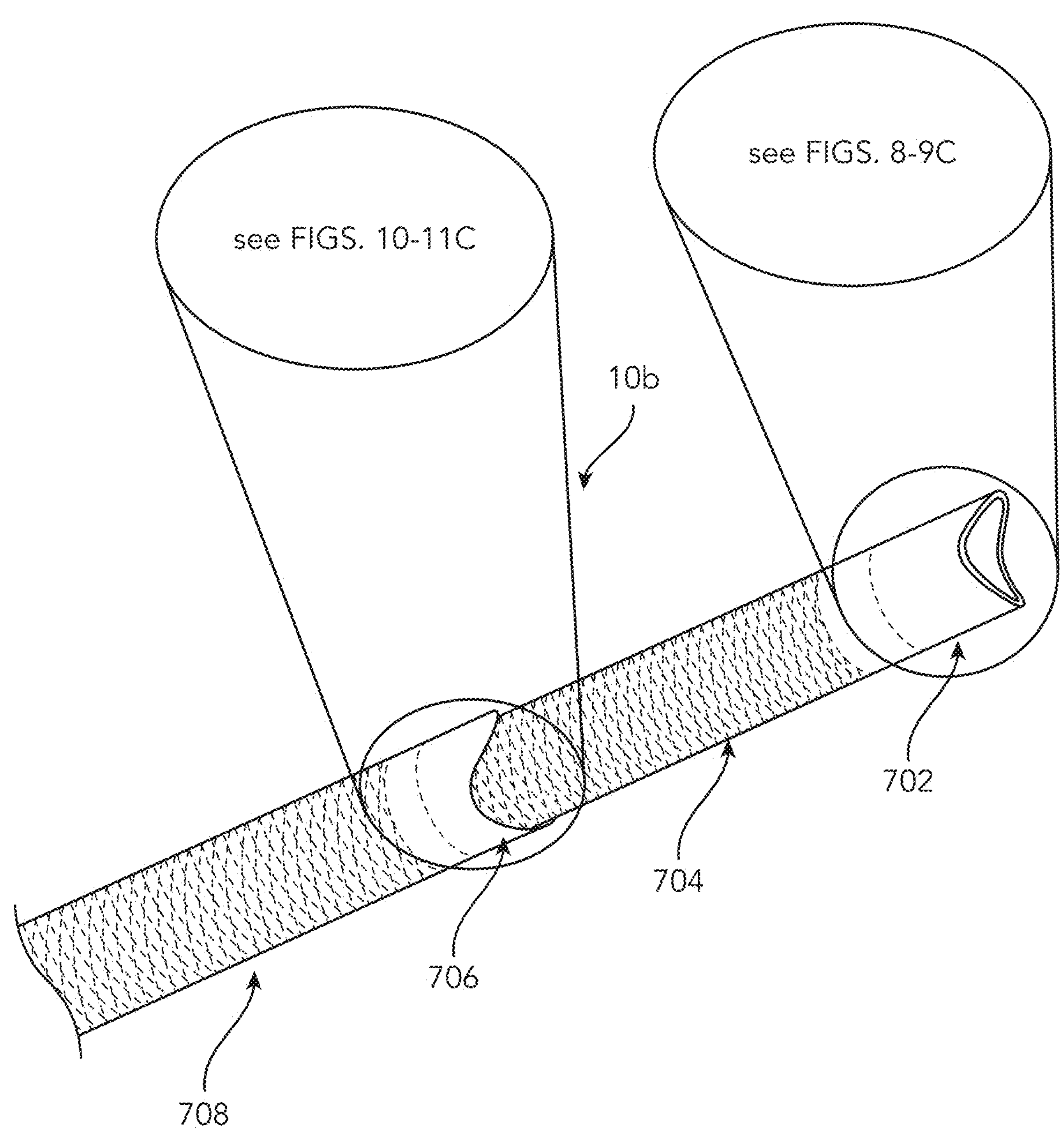
FIG. 7 illustrates a perspective view of a medical device including a catheter and a sheath, according to some embodiments.

FIG. 7 illustrates a perspective view of an aspiration device 10*b* including an aspiration head 702 and a delivery sheath 708, according to some embodiments. In some embodiments, the sheath 708 includes a sheath aspiration head 706. The sheath 708 may be sized and configured to deliver a catheter 704 to a target treatment site 20. In some embodiments, the sheath 708 is sized and configured to navigate larger vessel diameters, facilitating delivery of the catheter 704, while the catheter 704 is sized and configured to be delivered through the sheath 708 and through either the same vasculature as the sheath 708, or a smaller vasculature. In some embodiments, the catheter 704 and/or catheter aspiration head may be similar or substantially similar to the catheter 304 and/or aspiration head 302, as described herein.

Figure 8:
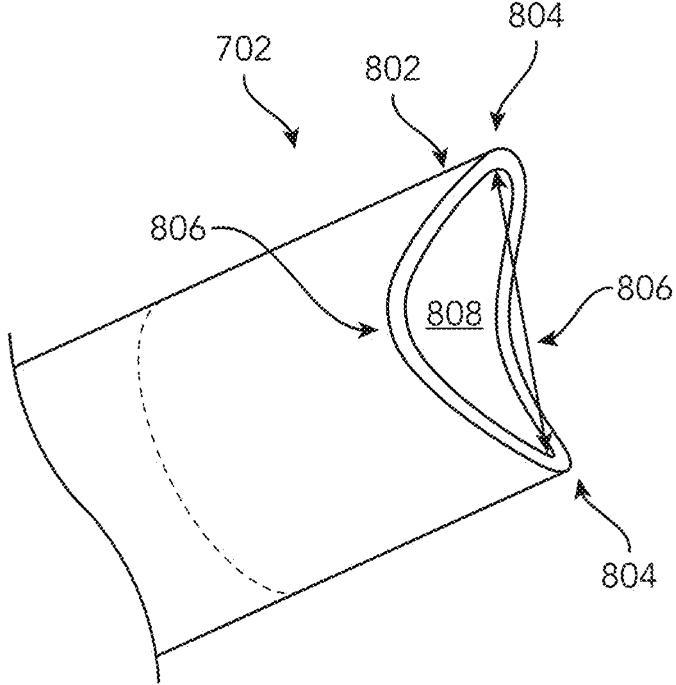
FIG. 8 illustrates a perspective view of the catheter of FIG. 7, according to some embodiments.
Figure 9A:
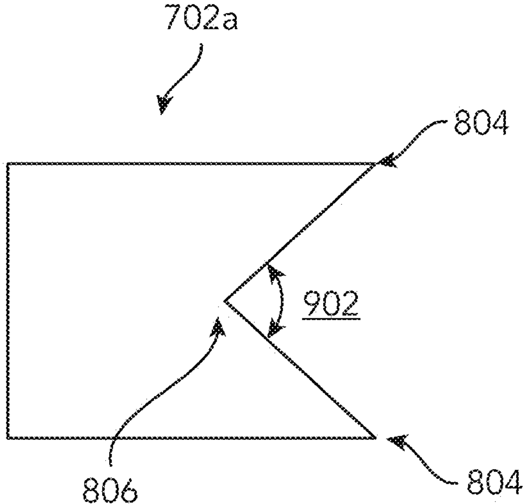
FIG. 9A illustrates a diagrammatic side view of a catheter aspiration head, according to some embodiments.
Figure 9B:
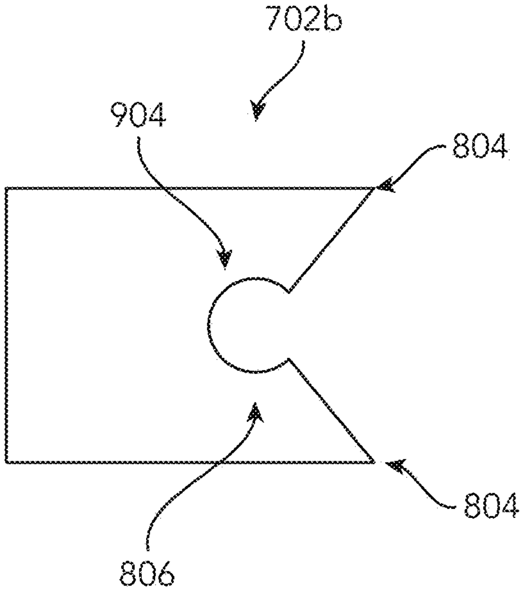
FIG. 9B illustrates a diagrammatic side view of another catheter aspiration head, according to some embodiments.
Figure 9C:
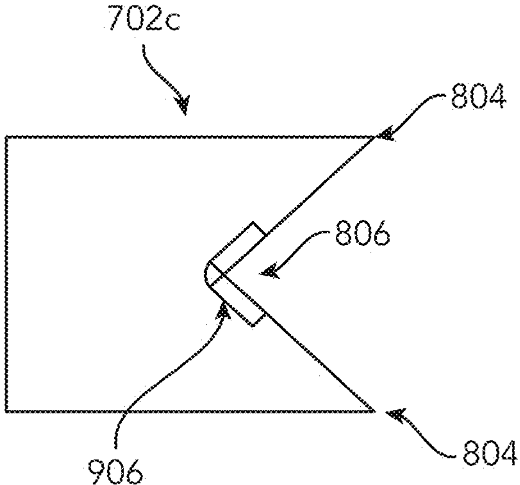
FIG. 9C illustrates a diagrammatic side view of another catheter aspiration head, according to some embodiments.

The catheter aspiration head 702 is illustrated and described in more detail in FIGS. 8-9C. The sheath aspiration head 706 is illustrated and described in more detail in FIGS. 10-11C. Either or both of the catheter aspiration head and the sheath aspiration head may be made from a polymer. Additionally or alternatively, either or both of the catheter and the sheath may be made from i) stainless steel, ii) nitinol, iii) PTFE, iv) polymer, or v) combinations thereof.

FIG. 8 illustrates a perspective view of the catheter aspiration head 702 of FIG. 7, according to some embodiments. FIG. 8 illustrates in more detail a catheter fishmouth 802 profile, showing the catheter peaks 804 and the catheter valleys 806. Generally, the catheter fishmouth 802 will include two catheter peaks 804 opposite one another, and two catheter valleys 806 opposite one another, the catheter valleys 806 between the catheter peaks 804 about the perimeter of the catheter fishmouth 802. In additional or alternative embodiments, more peaks and valleys may be included, creating an appearance akin to a saw wrapped in a circle.

Also illustrated in FIG. 8 is the catheter ID 808 of the catheter aspiration head 702. The catheter ID 808 of the catheter aspiration head 702 may be from about thirty thousandths of an inch to about one hundred and twelve thousandths of an inch. The catheter aspiration head 702 may be chosen based on the catheter ID 808 needed for the treatment of a vessel with a specific diameter, thereby maximizing the catheter ID 808 of the catheter aspiration head 702 that can be delivered through the vessel and contacting the occlusion. Additionally, an ID of the catheter 704 may be equal or at least substantially equal to the ID of the catheter aspiration head 702.

FIG. 9A illustrates a diagrammatic side view of a catheter aspiration head 702*a*, according to some embodiments. As shown in FIG. 9A, the catheter peaks 804 meet the catheter valleys 806 at an angle of extension 902. This angle of extension 902 may be the same, or different, between different catheter peaks 804 and different catheter valleys 806. For the purposes of FIG. 9A, it is assumed that the angle of extension 902 between the catheter peaks 804 and the catheter valleys 806 are the same.

The angle of extension 902 may be between about one degree and about one hundred and seventy-nine degrees. That is to say, any angle of extension 902 is considered in the present application between having an angle steep enough to include almost parallel lines, and having almost no angle. In smaller diameter embodiments, steeper angles may still meet each other in such a way as to facilitate contact with an occlusion. Similarly, in larger diameter embodiments, shallower angles may meet each other in such a way so as to facilitate greater contact with an occlusion than a flat-faced profile.

FIG. 9B illustrates a diagrammatic side view of another aspiration head, according to some embodiments. In this embodiment, the catheter aspiration head 702*b* continues to display the catheter peaks 804 and catheter valleys 806 of previous embodiments. However, in FIG. 9B, the catheter valleys 806 include an area of material weakness 904. This area of material weakness 904 may be a specific notch, or cut out, in the catheter valley 806 to allow the catheter valley 806 to at least partially collapse inward. In additional or alternative embodiments, the area of material weakness 904 is a material that is different, and more malleable/frangible than the surrounding material of the catheter aspiration head 702*b*.

In any embodiment, the area of material weakness 904 may permit the catheter peaks 804 to collapse at least partially inward in response to a force, such as the force of aspiration delivered through the medical device 10*b*. In permitting the catheter peaks 804 to collapse at least partially inward, greater contact with an occlusion 30 may occur, and, additionally or alternatively, a physical grip on the occlusion 30 may be had by the catheter peaks 804.

FIG. 9C illustrates a diagrammatic side view of another aspiration head, according to some embodiments. In this embodiment, the catheter aspiration head 702*c* continues to display the catheter peaks 804 and catheter valleys 806 of previous embodiments. However, in FIG. 9C, the catheter valleys 806 are coupled to/with a hinge 906. The hinge 906 may be combined with a material weakness in the catheter valley 806, such as the area of material weakness 904 of FIG. 9B. In additional or alternative embodiments, the material from which the catheter aspiration head 702*c* is made may be malleable enough to permit the catheter peaks 804 to collapse inward under force.

In any such embodiments, the hinge 906 may facilitate both the initiation of collapse of the catheter peaks 804 inward, as well as prevent too far of a collapse of the catheter peaks 804 in the case of a substantially malleable material due to any inherent force of the hinge (i.e., spring constant in a provided spring in the hinge 906) as well as a maximum permitted closure of the hinge 906. In permitting the catheter peaks 804 to collapse at least partially inward, greater contact with an occlusion 30 may occur, and, additionally or alternatively, a physical grip on the occlusion 30 may be had by the catheter peaks 804.

Figure 10:
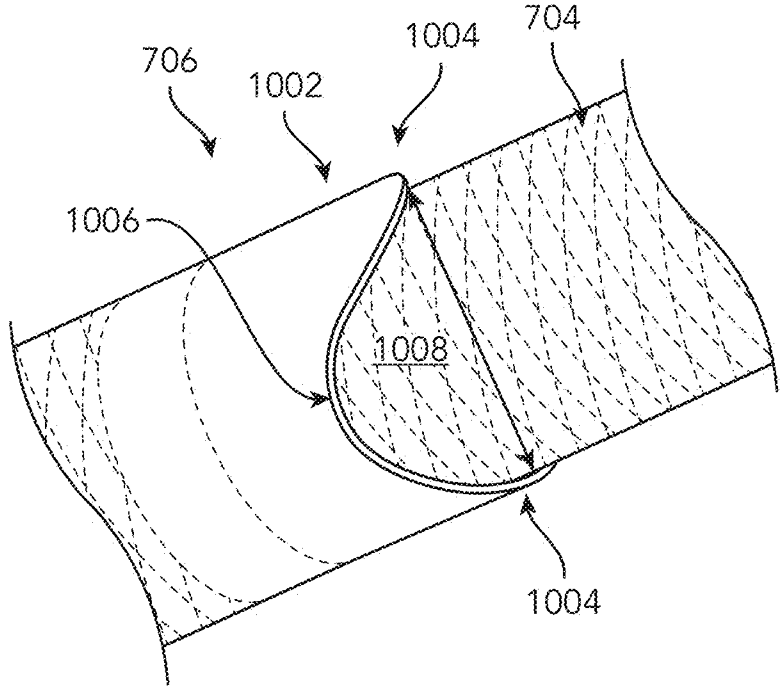
FIG. 10 illustrates a closer perspective view of the sheath and catheter of FIG. 7, according to some embodiments.

FIG. 10 illustrates a perspective view of the sheath 708 and sheath aspiration head 706 of FIG. 7, according to some embodiments. FIG. 10 illustrates in more detail a sheath fishmouth 1002 profile, showing the sheath peaks 1004 and the sheath valleys 1006. Generally, the sheath fishmouth 1002 will include two sheath peaks 1004 opposite one another, and two sheath valleys 1006 opposite one another, the sheath valleys 1006 between the peaks 1004 about the perimeter of the sheath fishmouth 1002. In additional or alternative embodiments, more peaks and valleys may be included, creating an appearance akin to a saw wrapped in a circle.

Also illustrated in FIG. 10 is the ID 1008 of the sheath aspiration head 706. The ID 1008 of the sheath aspiration head 706 may be from about thirty thousandths of an inch to about one hundred and twelve thousandths of an inch. The sheath aspiration head 706 may be chosen based on the ID 1008 needed for the treatment of a vessel with a specific diameter, thereby maximizing the ID 1008 of the sheath aspiration head 706 that can be delivered through the vessel and contacting the occlusion. Additionally, an ID of the sheath 708 may be equal or at least substantially equal to the ID of the sheath aspiration head 706.

As also illustrated in FIG. 10, a catheter 704 may travel through the sheath 708 and the sheath aspiration head 706 in order to egress the sheath 708 and the sheath aspiration head 706 and enter further and/or narrower vasculature. When the catheter 704 is within the sheath 708, the sheath aspiration head 706 may permit the medical device 10*b* to perform aspiration on an occlusion 30 without, or in tandem to, the aspiration capabilities of the catheter 704. This may permit for aspiration of occlusions 30 that are too large for the catheter 704. In some embodiments, the occlusion 30 is partially aspirated by the catheter 704, such that, when the catheter 704 is removed from the vessel, the occlusion 30 is removed as well.

In some embodiments, as described herein, aspiration is first performed using the sheath 708, prior to inserting the catheter 704 therethrough, followed by inserting the catheter 704 through the sheath 708, and performing aspiration using the catheter 704. Accordingly, this may permit for aspiration of occlusions 30 that are too large for the catheter 704. Moreover, the sheath may be used to remove occlusions at a first target treatment site, while the catheter is used to remove occlusions at a second target treatment site, or at a different area of the first target treatment site. Accordingly, the use of the sheath 708 and catheter 704 may be staggered.

Figure 11A:
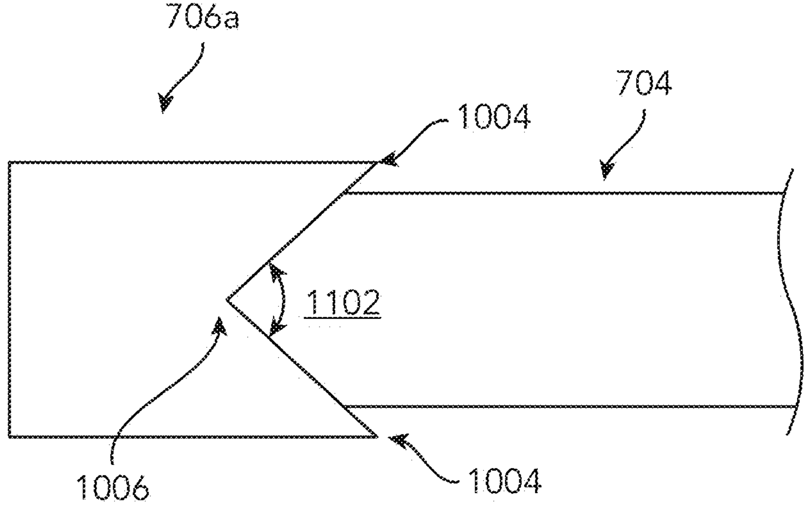
FIG. 11A illustrates a diagrammatic side view of a sheath aspiration head, according to some embodiments.

FIG. 11A illustrates a diagrammatic side view of an aspiration head, according to some embodiments. As shown in FIG. 11A, the sheath peaks 1004 meet the sheath valleys 1006 at an angle of extension 1102. This angle of extension 1102 may be the same, or different, between different sheath peaks 1004 and different sheath valleys 1006. For the purposes of FIG. 11A, it is assumed that the angle of extension 1102 between the sheath peaks 1004 and the sheath valleys 1006 are the same.

The angle of extension 1102 may be from about one degree to about one hundred and seventy-nine degrees. That is to say, any angle of extension 1102 is considered in the present application between having an angle steep enough to include almost parallel lines, and having almost no angle. In smaller diameter embodiments, steeper angles may still meet each other in such a way as to facilitate contact with an occlusion. Similarly, in larger diameter embodiments, shallower angles may meet each other in such a way so as to facilitate greater contact with an occlusion than a flat-faced profile.

Figure 11B:
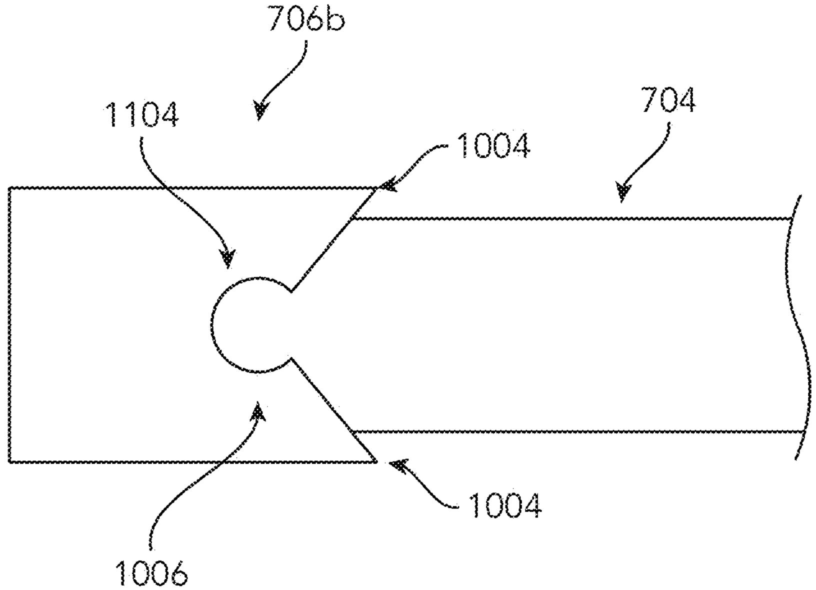
FIG. 11B illustrates a diagrammatic side view of another sheath aspiration head, according to some embodiments.

FIG. 11B illustrates a diagrammatic side view of another aspiration head, according to some embodiments. In this embodiment, the sheath aspiration head 706*b* continues to display the sheath peaks 1004 and sheath valleys 1006 of previous embodiments. However, in FIG. 11B, the sheath valleys 1006 include an area of material weakness 1104. This area of material weakness 1104 may be a specific notch, or cut out, in the sheath valley 1006 to allow the sheath valley 1006 to at least partially collapse inward. In additional or alternative embodiments, the area of material weakness 1104 is a material that is different, and more malleable/frangible than the surrounding material of the sheath aspiration head 706*b*.

In any embodiment, the area of material weakness 1104 may permit the sheath peaks 1004 to collapse at least partially inward in response to a force, such as the force of aspiration delivered through the medical device 10*b*. In permitting the sheath peaks 1004 to collapse at least partially inward, greater contact with an occlusion 30 may occur, and, additionally or alternatively, a physical grip on the occlusion 30 may be had by the sheath peaks 1004.

Figure 11C:
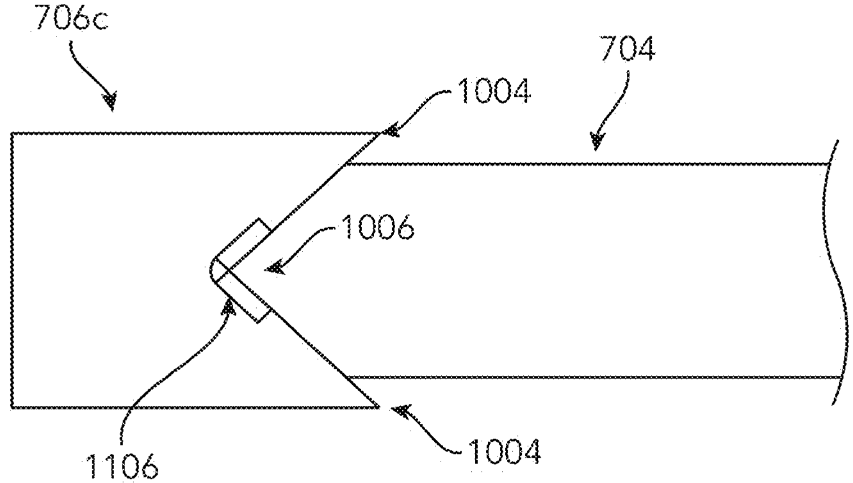
FIG. 11C illustrates a diagrammatic side view of another sheath aspiration head, according to some embodiments.

FIG. 11C illustrates a diagrammatic side view of another aspiration head, according to some embodiments. In this embodiment, the sheath aspiration head 706*c* continues to display the sheath peaks 1004 and sheath valleys 1006 of previous embodiments. However, in FIG. 11C, the sheath valleys 1006 are coupled to/with a hinge 1106. The hinge 1106 may be combined with a material weakness in the valley 1006, such as the area of material weakness 1104 of FIG. 11B. In additional or alternative embodiments, the material from which the sheath aspiration head 706*c* is made may be malleable enough to permit the sheath peaks 1004 to collapse inward under force.

In any such embodiments, the hinge 1106 may facilitate both the initiation of collapse of the sheath peaks 1004 inward, as well as prevent too far of a collapse of the sheath peaks 1004 in the case of a substantially malleable material due to any inherent force of the hinge (i.e., spring constant in a provided spring in the hinge 1106) as well as a maximum permitted closure of the hinge 1106. In permitting the sheath peaks 1004 to collapse at least partially inward, greater contact with an occlusion 30 may occur, and, additionally or alternatively, a physical grip on the occlusion 30 may be had by the sheath peaks 1004.

Figure 12:
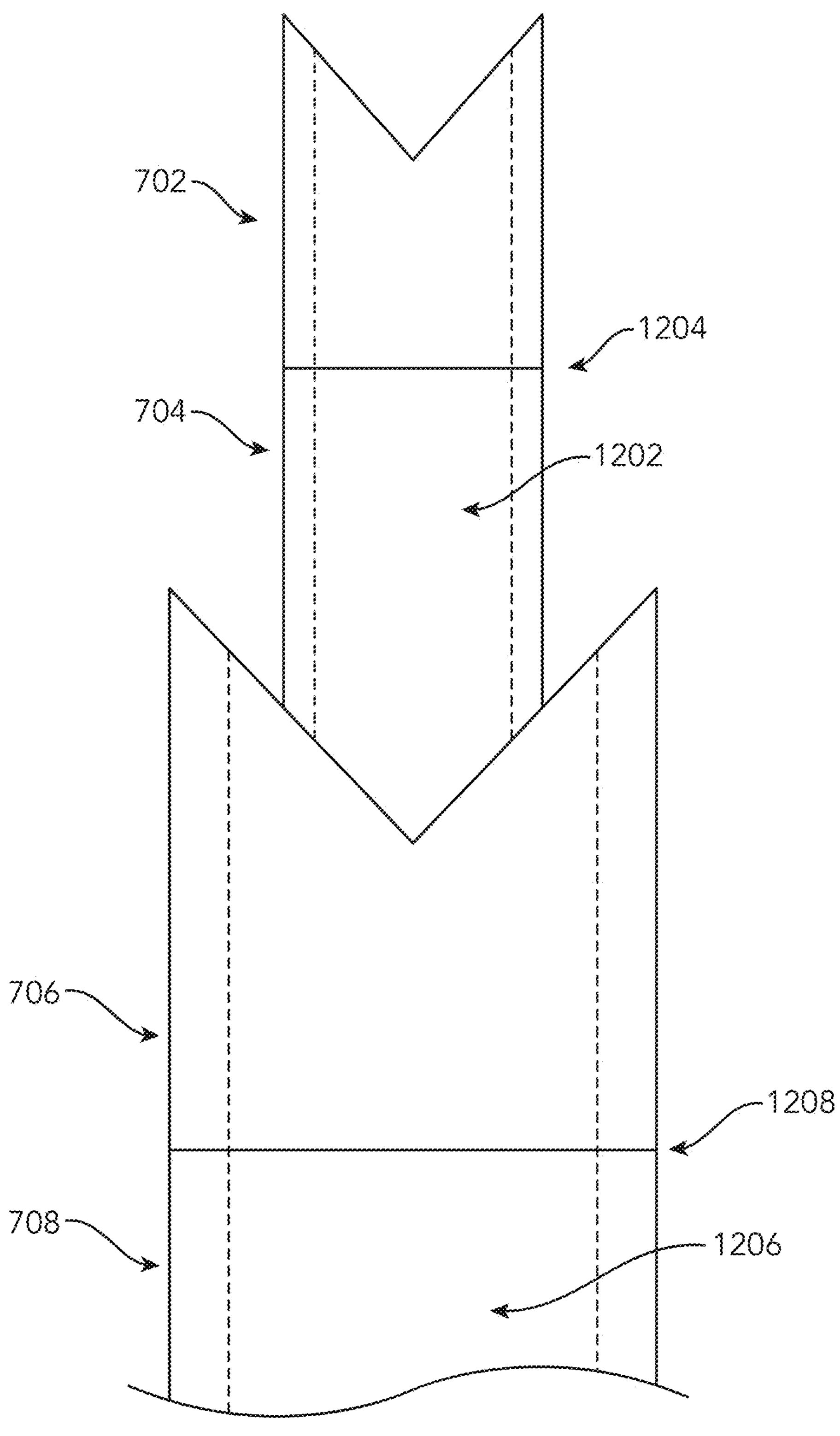
FIG. 12 illustrates a diagrammatic side view of the medical device of FIG. 7, according to some embodiments.

FIG. 12 illustrates a diagrammatic side view of the aspiration device of FIG. 7, according to some embodiments. As shown in FIG. 12, the aspiration device 10*b* includes the catheter aspiration head 702 as well as the catheter 704. Extending through both of the catheter 704 and the catheter aspiration head 702, an aspiration lumen 1202 is shown. The aspiration lumen 1202 may be the lumen through which an aspiration force is provided in order to aspirate an occlusion 30 from a target treatment site 20.

Also shown in FIG. 12 is a distal end 1204 where the catheter aspiration head 702 couples to the catheter 704. In some embodiments, the distal end 1204 is the distal end 1204 of the catheter 704. In additional or alternative embodiments, the catheter aspiration head 702 and the catheter 704 are a single structure. In such embodiments, distal end 1204 represents a portion of the medical device 10*b* where the catheter aspiration head 702 is considered to begin (i.e., the portion of the medical device 10*b* including catheter peaks 804 and catheter valleys 806) and where the catheter 704 portion is considered to terminate.

Further shown in FIG. 12, the aspiration device 10*b* includes the sheath aspiration head 706 as well as the delivery sheath 708. Extending through both of the sheath 708 and the sheath aspiration head 706, a delivery lumen 1206 is shown. The delivery lumen 1206 may be the lumen through which an aspiration force is provided in order to aspirate an occlusion 30 from a target treatment site 20 or a different target treatment site.

Also shown in FIG. 12 is a distal end 1208 where the sheath aspiration head 706 couples to the sheath 708. In some embodiments, the distal end 1208 is the distal end 1208 of the sheath 708. In additional or alternative embodiments, the sheath aspiration head 706 and the sheath 708 are a single structure. In such embodiments, distal end 1208 represents a portion of the medical device 10*b* where the sheath aspiration head 706 is considered to begin (i.e., the portion of the medical device 10*b* including sheath peaks 1004 and sheath valleys 1006) and where the sheath 708 portion is considered to terminate.

As expressed above, the sheath 708 may be sized and configured to deliver a catheter 704 to a target treatment site 20. In some embodiments, the sheath 708 is sized and configured to navigate larger vessel diameters, facilitating delivery of the catheter 704, while the catheter 704 is sized and configured to be delivered through the sheath 708 and through either the same vasculature as the sheath 708, or a smaller vasculature.

As also illustrated and described with respect to FIG. 10 above, the catheter 704 may travel through the sheath 708 and the sheath aspiration head 706 in order to egress the sheath 708 and the sheath aspiration head 706 and enter further and/or narrower vasculature. When the catheter 704 is within the sheath 708, the sheath aspiration head 706 may permit the medical device 10*b* to perform aspiration on an occlusion 30 without, or in tandem to, the aspiration capabilities of the catheter 704. This may permit for aspiration of occlusions 30 that are too large for the catheter 704. In some embodiments, the occlusion 30 is partially aspirated by the catheter 704, such that, when the catheter 704 is removed from the vessel, the occlusion 30 is removed as well.

In some embodiments, as described herein, aspiration is first performed using the sheath 708, prior to inserting the catheter 704 therethrough, followed by inserting the catheter 704 through the sheath 708, and performing aspiration using the catheter 704. Accordingly, this may permit for aspiration of occlusions 30 that are too large for the catheter 704. Moreover, the sheath may be used to remove occlusions at a first target treatment site, while the catheter is used to remove occlusions at a second target treatment site, or at a different area of the first target treatment site. Accordingly, the use of the sheath 708 and catheter 704 may be staggered.

Figure 13:
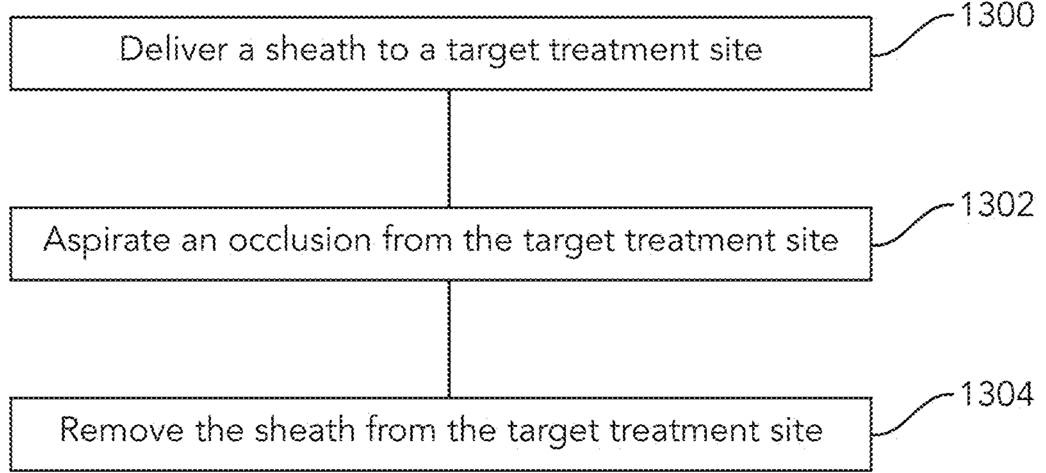
FIG. 13 illustrates a flowchart depicting a method of aspirating an occlusion, according to some embodiments.

FIG. 13 illustrates a flowchart depicting a method of aspirating an occlusion, according to some embodiments. In some embodiments, the method includes delivering a sheath to a target treatment site (at step 1300). The sheath may include a profiled shape, such as a fishmouth shape, such as to facilitate delivery of the sheath to the target treatment site without ensnaring or otherwise penetrating a vessel wall or vascular junction. The sheath may be any sheath described herein, which may include delivery sheath 708, which may include a sheath aspiration head 706 having the fishmouth shape.

According to some embodiments, the method includes aspirating an occlusion from the target treatment site (at step 1302). A fishmouth profile may increase the points of contact of the sheath with the occlusion, thereby increasing the efficacy of the aspiration capabilities of the medical device. The method may include removing the sheath from the target treatment site (at step 1304).

Figure 14:
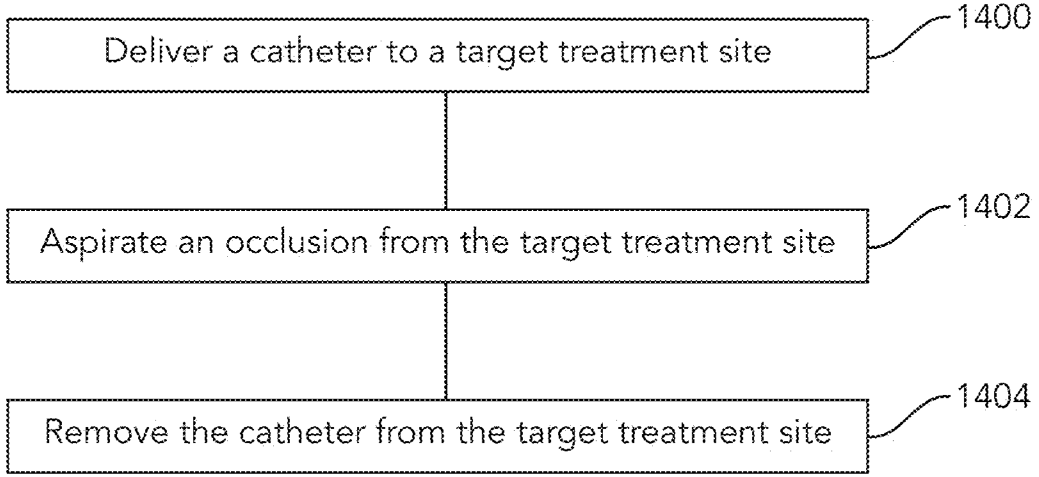
FIG. 14 illustrates a flowchart depicting another method of aspirating an occlusion, according to some embodiments.

FIG. 14 illustrates a flowchart depicting another method of aspirating an occlusion, according to some embodiments. In some embodiments, the method includes delivering a catheter to a target treatment site (at step 1400). The catheter may include a profiled shape, such as a fishmouth shape, such as to facilitate delivery of the catheter to the target treatment site without ensnaring or otherwise penetrating a vessel wall or vascular junction. The catheter may be delivered through a delivery lumen of a sheath (e.g., 708 as described herein), when the medical device includes a sheath and a catheter. Additionally or alternatively, the target treatment site for which the catheter is delivered to may be a second target treatment site that is distinct from the treatment site being treated by the sheath in steps 1300, 1302, and 1304 above.

The catheter may be any catheter described herein, which may include catheter 304, 704, and which may include an aspiration head 302, 702 having the fishmouth shape.

According to some embodiments, the method includes aspirating an occlusion from the target treatment site (at step 1402). A fishmouth profile may increase the points of contact of the sheath with the occlusion, thereby increasing the efficacy of the aspiration capabilities of the medical device. In the case of a second target treatment site as described in the preceding paragraph, the occlusion may additionally or alternatively be a second occlusion, wherein the first occlusion is the occlusion aspirated by the sheath in step 1302 above.

The method may include removing the catheter from the target treatment site (at step 1404). In embodiments where the catheter is delivered through a delivery lumen of a sheath, the catheter may be removed, via the delivery lumen, prior to removal of the sheath.

In some embodiments, steps 1300-1304 are performed using the sheath at a first target treatment site, or a first portion of a target treatment site, while steps 1400-1404 are subsequently performed for a second target treatment site or a second portion of a target treatment site. Accordingly, the sheath and catheter may be used for aspiration in a staggered configuration.

Figure 15:
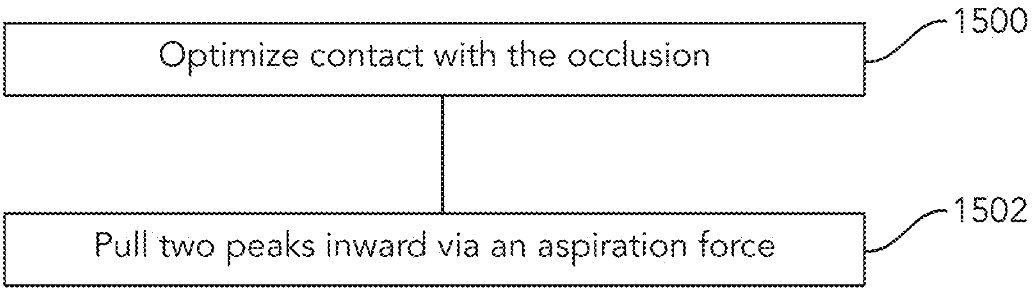
FIG. 15 illustrates a flowchart depicting a method of increasing contact with an occlusion, according to some embodiments.

FIG. 15 illustrates a flowchart depicting a method of increasing contact with an occlusion, according to some embodiments. In some embodiments, the method includes optimizing contact with the occlusion (at step 1500). The aspiration head may define a perimeter including two peaks located at opposite ends of the aspiration head from one another, and two valleys each located between the two peaks about the perimeter, the two valleys located at opposite ends of the aspiration head from one another. The aspiration head may be a catheter aspiration head or a sheath aspiration as illustrated and described throughout the present disclosure.

With respect to an aspiration head, a catheter aspiration head, and/or a sheath aspiration head as illustrated and described throughout the present disclosure, at least one of the two valleys may include an area of material weakness. Additionally or alternatively, the medical device may further include a hinge located on an inside or an outside of i) one or ii) both of the two valleys. In either case, according to some embodiments, the method includes pulling two peaks inward via an aspiration force (at step 1502). The steps 1500-1502 may be used with any method described in FIGS. 13-14.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1, and embodiments described in other sections may apply to and be combined with embodiments described within the "Topic 1" section.

To increase the clarity of various features, other features are not labeled in each figure.

The various features and processes described above may be used independently of one another or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, parallel, or some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless expressly stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless expressly stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "substantially" refers to less than or equal to +/−1%, +/−2%, +/−3%, +/−4%, +/−5%, +/−6%, +/−7%, +/−8%, +/−9%, +/−10%, +/−11%, +/−12%, +/−14%, or +/−15% variation. As a non-limiting example, substantially parallel represents a range of −1 to 1 degree difference, −5 to 5 degree difference, or −15 degrees to 15 degrees of difference from being parallel, depending on the embodiments.

While certain example embodiments have been described, these embodiments have been presented by way of example only and are not intended to limit the scope of the inventions disclosed herein. Thus, nothing in the foregoing description implies that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

We claim:

1. A medical device, comprising:

a catheter, comprising an aspiration lumen;

an aspiration head located at a distal end of the catheter, the aspiration head comprising a catheter fishmouth; and a sheath comprising a delivery lumen through which the catheter is configured to extend, wherein the sheath comprises a sheath aspiration head located at a distal end of the sheath, the sheath aspiration head comprising a sheath fishmouth, and wherein the sheath aspiration head is made from a polymer.

2. The medical device of claim 1, wherein the catheter fishmouth defines a perimeter comprising:

two peaks located at opposite ends of the aspiration head from one another; and two valleys each located between the two peaks about the perimeter, the two valleys located at opposite ends of the aspiration head from one another.

3. The medical device of claim 2, wherein at least one of the two valleys comprises an area of material weakness, such that, when aspiration is performed through the catheter, the two peaks are pulled inward with respect to one another.

4. The medical device of claim 2, further comprising a hinge located on an inside or an outside of i) one or ii) both of the two valleys, the hinge configured to permit the two peaks to be pulled inward with respect to one another while aspiration is performed through the catheter.

5. The medical device of claim 2, wherein the two peaks extend from the two valleys at an angle from about one degree to about one hundred and seventy-nine degrees.

6. The medical device of claim 1, wherein the aspiration head is made from a polymer.

7. The medical device of claim 1, wherein the catheter is made from i) stainless steel, ii) nitinol, iii) Polytetrafluoroethylene (PTFE), iv) polymer, or v) combinations thereof.

8. The medical device of claim 1, wherein the catheter fishmouth defines a perimeter comprising:

two peaks located at opposite ends of the aspiration head from one another; and two valleys each located between the two peaks about the perimeter, the two valleys located at opposite ends of the aspiration head from one another, wherein the two peaks are two catheter peaks, wherein the two valleys are two catheter valleys, and wherein the sheath fishmouth defines a perimeter having:

two sheath peaks located at opposite ends of the sheath aspiration head from one another; and two sheath valleys each located between the two sheath peaks about the sheath fishmouth perimeter, the two sheath valleys located at opposite ends of the sheath aspiration head from one another.

9. The medical device of claim 8, wherein at least one of the two sheath valleys comprises an area of material weakness, such that, when aspiration is performed through the sheath, the two sheath peaks are pulled inward with respect to one another.

10. The medical device of claim 8, further comprising a hinge located on an inside or an outside of i) one or ii) both of the two sheath valleys, the hinge configured to permit the two sheath peaks to be pulled inward with respect to one another while aspiration is performed through the sheath.

11. A medical device, comprising:

a catheter, comprising an aspiration lumen;

an aspiration head located at a distal end of the catheter, the aspiration head comprising a catheter fishmouth; and a sheath comprising a delivery lumen through which the catheter is configured to extend, wherein the sheath comprises a sheath aspiration head located at a distal end of the sheath, the sheath aspiration head comprising a sheath fishmouth, and wherein the sheath is made from i) stainless steel, ii) nitinol, iii) PTFE, iv) polymer, or v) combinations thereof.

12. The medical device of claim 11, wherein the catheter fishmouth defines a perimeter comprising:

two peaks located at opposite ends of the aspiration head from one another; and two valleys each located between the two peaks about the perimeter, the two valleys located at opposite ends of the aspiration head from one another.

13. The medical device of claim 12, wherein at least one of the two valleys comprises an area of material weakness, such that, when aspiration is performed through the catheter, the two peaks are pulled inward with respect to one another.

14. The medical device of claim 12, further comprising a hinge located on an inside or an outside of i) one or ii) both of the two valleys, the hinge configured to permit the two peaks to be pulled inward with respect to one another while aspiration is performed through the catheter.

15. The medical device of claim 12, wherein the two peaks extend from the two valleys at an angle from about one degree to about one hundred and seventy-nine degrees.

16. The medical device of claim 11, wherein the aspiration head is made from a polymer.

17. The medical device of claim 11, wherein the catheter is made from i) stainless steel, ii) nitinol, iii) Polytetrafluoroethylene (PTFE), iv) polymer, or v) combinations thereof.

18. The medical device of claim 11, wherein the catheter fishmouth defines a perimeter comprising:

two peaks located at opposite ends of the aspiration head from one another; and two valleys each located between the two peaks about the perimeter, the two valleys located at opposite ends of the aspiration head from one another, wherein the two peaks are two catheter peaks, wherein the two valleys are two catheter valleys, and wherein the sheath fishmouth defines a perimeter having:

two sheath peaks located at opposite ends of the sheath aspiration head from one another; and two sheath valleys each located between the two sheath peaks about the sheath fishmouth perimeter, the two sheath valleys located at opposite ends of the sheath aspiration head from one another.

19. The medical device of claim 18, wherein at least one of the two sheath valleys comprises an area of material weakness, such that, when aspiration is performed through the sheath, the two sheath peaks are pulled inward with respect to one another.

20. The medical device of claim 18, further comprising a hinge located on an inside or an outside of i) one or ii) both of the two sheath valleys, the hinge configured to permit the two sheath peaks to be pulled inward with respect to one another while aspiration is performed through the sheath.

* * * * *